US012105071B2

(12) United States Patent
Kolvek et al.

(10) Patent No.: US 12,105,071 B2
(45) Date of Patent: Oct. 1, 2024

(54) MULTI-ELEMENT, ULTRA-LOW SWAP CHEMICAL PRE-CONCENTRATOR

(71) Applicant: BAE SYSTEMS Information and Electronic Systems Integration Inc., Nashua, NH (US)

(72) Inventors: Edward M. Kolvek, Merrimac, MA (US); Pierre-Alain S. Auroux, Rockville, MD (US); Don A. Harris, Columbia, MD (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 560 days.

(21) Appl. No.: 16/719,122

(22) Filed: Dec. 18, 2019

(65) Prior Publication Data
US 2021/0190746 A1    Jun. 24, 2021

(51) Int. Cl.
| *G01N 33/00* | (2006.01) |
|---|---|
| *G01N 1/14* | (2006.01) |
| *G01N 1/24* | (2006.01) |
| *G01N 1/40* | (2006.01) |

(52) U.S. Cl.
CPC ........... *G01N 33/0011* (2013.01); *G01N 1/14* (2013.01); *G01N 1/405* (2013.01); *G01N 2001/245* (2013.01); *G01N 33/0019* (2024.05)

(58) Field of Classification Search
CPC .... G01N 1/14; G01N 1/405; G01N 2001/245; G01N 2033/0019; G01N 33/0011; G01N 1/2214; G01N 1/2273; G01N 2001/2223
USPC .............................. 73/863.21, 863.11, 863.85
See application file for complete search history.

(56) References Cited

U.S. PATENT DOCUMENTS

| 5,691,206 A | 11/1997 | Pawliszyn |
|---|---|---|
| 5,693,228 A | 12/1997 | Koehler et al. |
| 6,164,144 A | 12/2000 | Berg |
| 6,171,378 B1 | 1/2001 | Manginell et al. |
| 6,527,835 B1 | 3/2003 | Manginell et al. |
| 7,118,712 B1 | 10/2006 | Manginell et al. |

(Continued)

FOREIGN PATENT DOCUMENTS

| WO | WO-2015069341 A2 * | 5/2015 | ............. G01N 1/405 |
|---|---|---|---|
| WO | WO-2016103561 A1 * | 6/2016 | ............. B01D 53/04 |
| WO | 2017/204636 A2 | 11/2017 | |

OTHER PUBLICATIONS

International Search Report Corresponding to PCT/US2018/049486 mailed Nov. 6, 2018.

(Continued)

*Primary Examiner* — Daniel S Larkin
*Assistant Examiner* — Nashmiya S Fayyaz
(74) *Attorney, Agent, or Firm* — Gary McFaline; KPIP Law, PLLC

(57) ABSTRACT

The system and method for a multi-element, ultra-low SWaP chemical concentrator incorporating Applicant's own open cell foamed adsorbent material which allows high volume sampling (e.g., liters per minute) to achieve low detection limits (ppt) using high-volume, low-pressure air sources (i.e. fans or blowers) rather than pumps. The device delivers the sample directly to an analyzer without the need for a typical intermediate cryogenic trapping step. In one example, a rotary style concentrator comprises four individual foam elements. Each element can be individually heated to desorb analytes.

16 Claims, 6 Drawing Sheets

(56) References Cited

U.S. PATENT DOCUMENTS

| | | |
|---|---|---|
| 7,299,711 B1 | 11/2007 | Linker et al. |
| 7,776,615 B2 | 8/2010 | Yuka et al. |
| 7,931,788 B1 | 4/2011 | Wilkins |
| 8,365,575 B2 | 2/2013 | Kippeny |
| 8,715,396 B1 | 5/2014 | Kippeny et al. |
| 9,558,926 B2 | 1/2017 | Musselman |
| 2003/0085348 A1 | 5/2003 | Megerle |
| 2004/0131503 A1 | 7/2004 | McGann et al. |
| 2004/0157342 A1 | 8/2004 | Lovell et al. |
| 2011/0188702 A1 | 8/2011 | Haas et al. |
| 2014/0017158 A1 | 1/2014 | Sengupta et al. |
| 2014/0251134 A1 | 9/2014 | Sengupta et al. |
| 2017/0054050 A1 | 2/2017 | Mader et al. |
| 2019/0041305 A1* | 2/2019 | Bowers, II ............... G01N 1/02 |

OTHER PUBLICATIONS

Pelissier et al., "Silicon Carbide Heating Elements", Ceramics International, 24 (1998) pp. 371-377.

* cited by examiner

MULTI-ELEMENT, ULTRA-LOW SWAP CHEMICAL PRE-CONCENTRATOR

FIELD OF THE DISCLOSURE

The present disclosure relates to chemical pre-concentrators and more particularly to a multi-element, ultra-low SWaP chemical pre-concentrator.

BACKGROUND OF THE DISCLOSURE

Long term autonomous and continuous monitoring of an airborne chemical environment has become a priority for various applications. The size, weight, and power (SWaP) requirements of prior systems are not compatible with such requirements.

Wherefore it is an object of the present disclosure to overcome the above-mentioned shortcomings and drawbacks associated with the conventional chemical pre-concentrators.

SUMMARY OF THE DISCLOSURE

One aspect of the present disclosure is a system comprising a chemical pre-concentrator, comprising: a housing configured to hold an array of chemical pre-concentrator element cartridges distributed about a central axis; and a top cover and a bottom cover of the housing being configured to move using a sliding caliper mechanism, by way of a linear actuator; each cartridge comprising: a carbide-derived carbon (CDC) foam element; dielectric/thermal insulators; electrodes; and an elastomer seal; wherein the top and the bottom covers slide to open the chemical pre-concentrator during analyte sample collection and to close the chemical pre-concentrator for analyte sample delivery, energizing the electrodes in a cartridge, heats the foam element to desorb the analytes, and each cartridge is controlled independently and is separately sealed during desorption to avoid bleed of analytes to other cartridges.

One embodiment of the chemical pre-concentrator is wherein the linear actuator is used to expand the top cover away from the bottom cover to provide for gaps allowing a flow of air, or other gas, to flow past the element cartridges.

In certain embodiments, the array comprises four CDC foam element cartridges.

Another embodiment of the chemical pre-concentrator is wherein during analyte sample collection a low impedance air flow path is provided so that ambient air can be independently drawn through each element cartridge to enable collection of the chemical analytes. In some cases, the low impedance airflow path enables both high flow and very low fan/blower power consumption during sample collection.

Yet another embodiment of the chemical concentrator further comprises fans/blowers to push/pull air flow through the element cartridges. In certain embodiments, the chemical pre-concentrator further comprises inlets for carrier gas delivery lines and outlets for sample delivery lines used when attaching the pre-concentrator to an analyzer.

Still yet another embodiment of the chemical pre-concentrator is wherein the element cartridge further comprises a series of springs with pre-loaded adjustments to facilitate pressing spring pressure plates against high temperature insulators on each side of the foam element, to cause a pair of energized electrodes to contact the CDC foam element in a desorption step.

Another aspect of the present disclosure is a method of collecting chemical analytes, comprising: providing a chemical pre-concentrator, comprising: a housing configured to hold an array of chemical pre-concentrator element cartridges distributed about a central axis; and a top cover and a bottom cover of the housing being configured to move using a sliding caliper mechanism, by way of a linear actuator; each cartridge comprising: a CDC foam element; dielectric/thermal insulators; electrodes; and an elastomer seal; sliding the top and the bottom covers to open the chemical pre-concentrator; engaging one or more fans/blowers to create an air flow over the element cartridges during analyte sample collection; capturing the analyte sample with the element cartridges; and sliding the top and the bottom covers to close the chemical pre-concentrator.

One embodiment of the method of collecting chemical analytes is wherein the array comprises four element cartridges. In some cases, a linear actuator is used to expand the top cover away from the bottom cover to provide for gaps allowing a flow of air, or other gas, to flow past the element cartridges.

Another embodiment of the method of collecting chemical analytes is wherein during analyte sample collection a low impedance air flow path is provided so that ambient air can be independently drawn through each element cartridge to enable collection of the chemical analytes. In some cases, the chemical pre-concentrator further comprises fans/blowers to push/pull air flow through the element cartridges. In certain embodiments, the chemical pre-concentrator further comprises inlets for carrier gas delivery lines and outlets for sample delivery lines used when attaching the pre-concentrator to an analyzer.

Yet another aspect of the present disclosure is a method of delivering chemical analytes to a chemical analyzer for analysis, comprising: providing a chemical pre-concentrator, comprising: a housing configured to hold an array of chemical pre-concentrator element cartridges distributed about a central axis; inlets for carrier gas delivery lines and outlets for sample delivery; and a top cover and a bottom cover of the housing being configured to move using a sliding caliper mechanism, by way of a linear actuator; each cartridge comprising: a CDC foam element; dielectric/thermal insulators; electrodes; and an elastomer seal; energizing the electrodes in a cartridge; heating the foam element to desorb the analytes, wherein each element cartridge is controlled independently and is separately sealed during desorption to avoid bleed of analytes to other cartridges; switching a switched gas valve to deliver a burst of pressurized carrier gas to drive the analytes towards the chemical analyzer inlet by flowing through the foam element and out the sample delivery line to the chemical analyzer.

One embodiment of the method of delivering chemical analytes to a chemical analyzer for analysis is wherein a high temperature insulator is used around the CDC foam element to keep heat applied to the CDC foam element via an energized electrode from spreading throughout the remainder of the system or to the rest of the device. In some cases, a temperature applied to the CDC foam element for desorption is about 350° C.

Another embodiment of the method of delivering chemical analytes to a chemical analyzer for analysis is wherein the element cartridge further comprises a series of springs with pre-load adjustments to facilitate pressing spring pressure plates against high temperature insulators on each side of the foam element, to cause a pair of energized electrodes to contact the CDC foam element in a desorption step. In certain embodiments the chemical pre-concentrator further comprising fans/blowers to push/pull air flow through the element cartridges. In some cases, the array comprises four element cartridges.

These aspects of the disclosure are not meant to be exclusive and other features, aspects, and advantages of the present disclosure will be readily apparent to those of ordinary skill in the art when read in conjunction with the following description, appended claims, and accompanying drawings.

BRIEF DESCRIPTION OF THE DRAWINGS

The foregoing and other objects, features, and advantages of the disclosure will be apparent from the following description of particular embodiments of the disclosure, as illustrated in the accompanying drawings in which like reference characters refer to the same parts throughout the different views. The drawings are not necessarily to scale, emphasis instead being placed upon illustrating the principles of the disclosure.

DETAILED DESCRIPTION OF THE DISCLOSURE

One embodiment of the present disclosure is a device that forms the front-end collection stage for an ultra-low-power chemical analysis capability for the detection and identification of hazardous chemicals, explosives, chemical weapons, narcotics, industrial toxins and pollutants, and the like. The device of the present disclosure utilizes an embodiment of Carbide Derived Carbon or CDC foam element. In certain cases, the CDC foam element is functionalized to target distinct groups of chemical threats. In one embodiment, four elements are arranged in an array of multiple sampling elements. The CDC foam element array is packaged into a low SWaP, multi-element sampling device that enables highly efficient collection and delivery of chemical samples. In some cases, low-SWaP includes a hand-held device. In certain cases, the low-SWaP device is stationary.

In one embodiment, the technology used in the device of the present disclosure is Applicant's open cell foam adsorbent material which allows high volume sampling (e.g., liters per minute) to achieve low detection limits (ppt) using high-volume, low-pressure air sources (i.e. fans or blowers) rather than pumps. The device delivers the sample directly to an analyzer without the need for a typical intermediate cryogenic trapping step.

In certain embodiments, top and bottom plates are moved by a linear actuator to provide scaling around a CDC foam element insert through clamping. This approach utilizes static seals which have inherent advantages over dynamic, sliding seals in that energy is not consumed overcoming sliding seal friction. Additionally, lubrication is not required and reduced seal wear enables improved longevity of the sealing rings. This concept also enables a radial arrangement of multiple collection units (four nominally).

In one embodiment, each collection unit is sealed from the other collection units to prevent analyte bleed to the other sites. Each collection unit CDC foam element can be triggered independently for collection or desorption. In some cases, top and bottom plates slide vertically to open the pre-concentrator during sampling and close the pre-concentrator during desorption.

The device of the present disclosure is both compact and efficient from a power consumption standpoint. It is also scalable to enable a varying quantity of functionalized CDC foam elements. In one embodiment, a single linear actuator is used to selectively place all sensing elements in either an adsorb or a desorb position. This is accomplished without expending energy against the friction associated with sliding seals of conventional samplers. It also enables both low impedance air flow for sampling and high concentration sample bolus delivery to a chemical analyzer. In addition, the packaging concept provides a compliant method for producing electrical contact with the CDC foam element to enable heating which has been shown to extend the life of the element.

Figure 1:
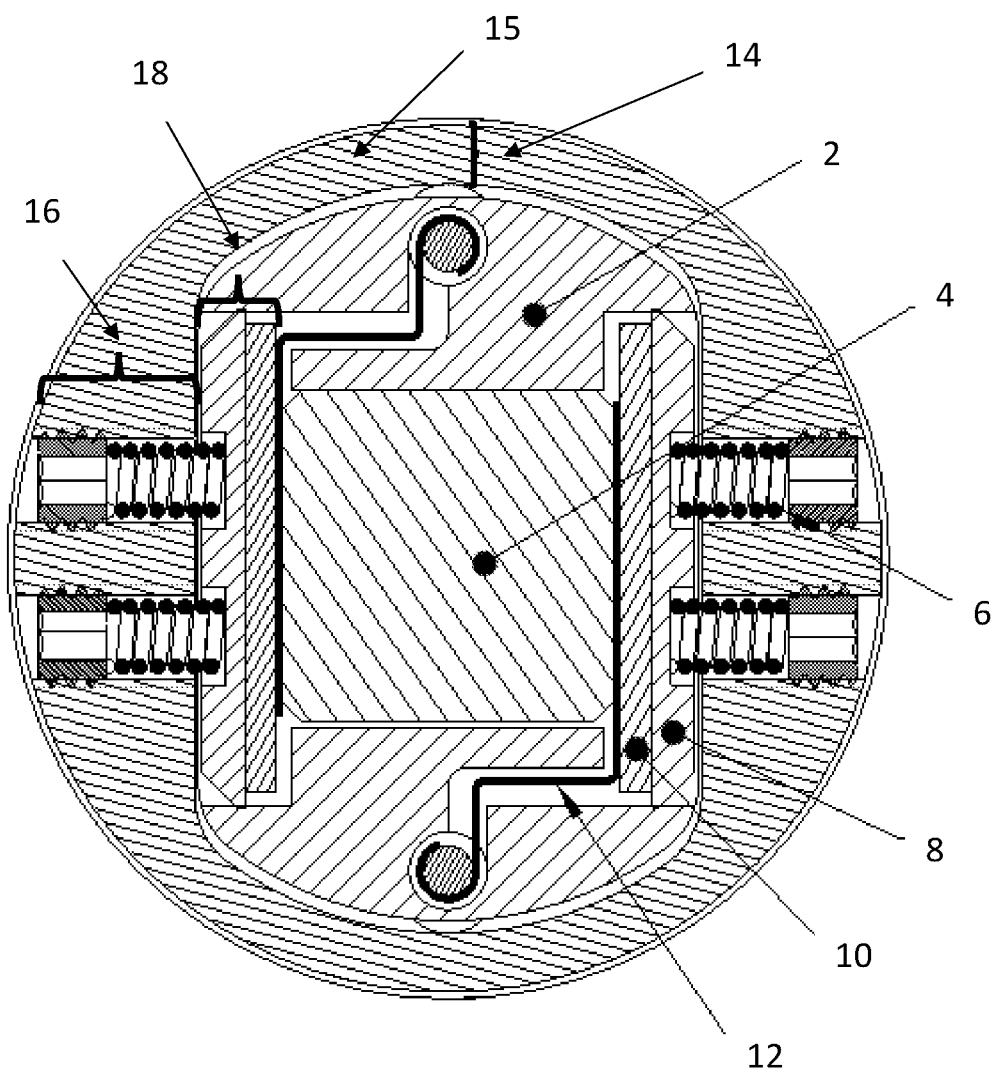
FIG. 1 is a diagram of one embodiment of a carbide-derived carbon (CDC) foam element assembly for a multi-element, ultra-low swap chemical pre-concentrator according to the principles of the present disclosure.

Referring to FIG. 1, a diagram of a top view of one embodiment of a carbide-derived carbon (CDC) foam element assembly for a multi-element, ultra-low SWaP chemical pre-concentrator according to the principles of the present disclosure is shown. More specifically, a housing high temperature insulator 2 is used around the CDC foam element 4. In some cases, the insulator is a ceramic ring. This helps to keep any heat applied to the CDC foam element via an energized electrode 12 from spreading throughout the remainder of the system or to the rest of the device. In some embodiments, the temperature applied to the CDC foam element for desorption is about 350° C.

Figure 2:
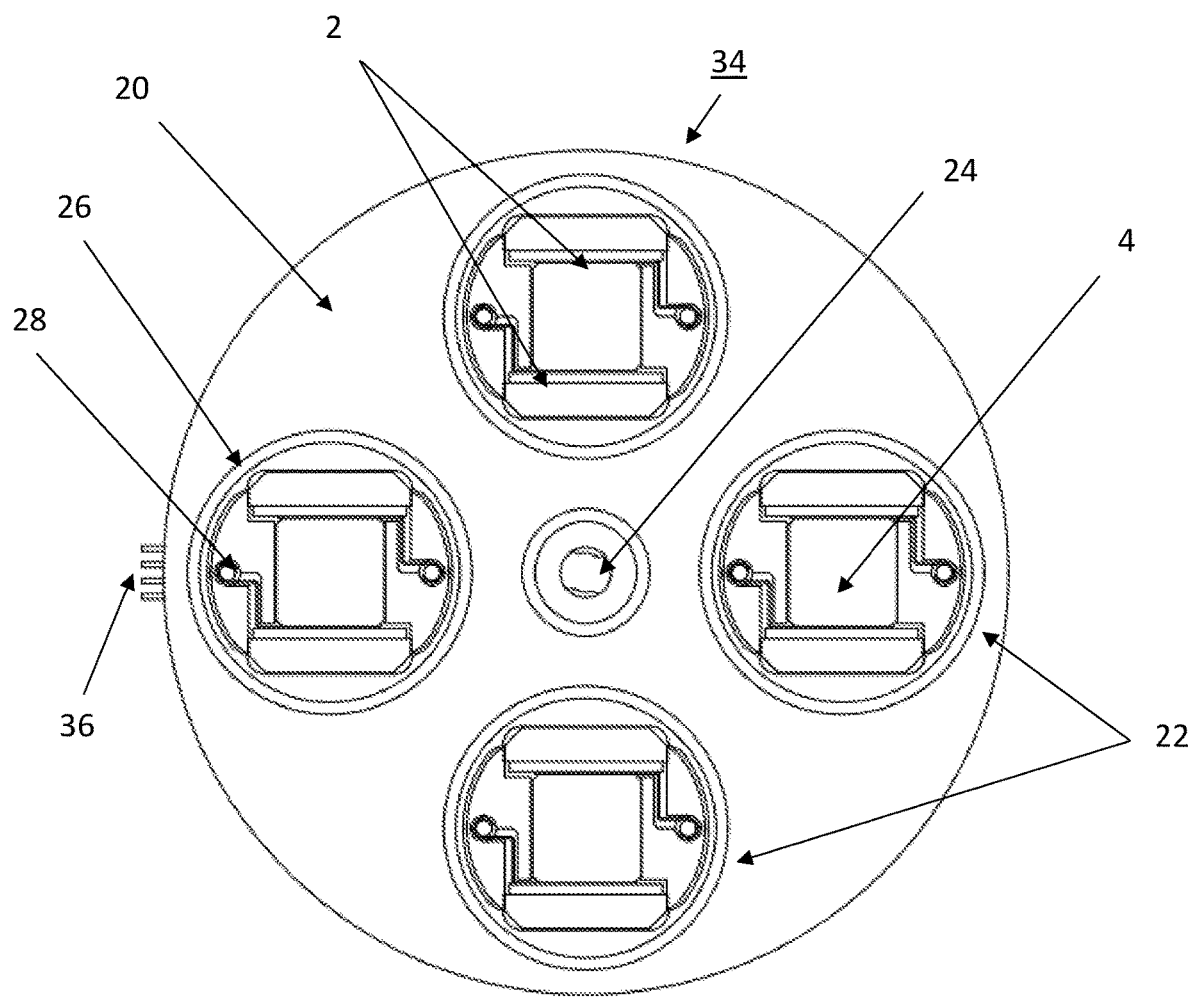
FIG. 2 is a diagram of one embodiment of a radial arrangement for a multi-element, ultra-low swap chemical pre-concentrator according to the principles of the present disclosure.

Still referring to FIG. 1, a series of springs 6 with pre-load adjustments are used to facilitate pressing spring pressure plates 8 against high temperature insulator plates 10 on each side of the CDC foam element insert, to cause a pair of energized electrodes 12 to contact the CDC foam element 4 in a desorption step. In this embodiment, an electrical current is applied to the electrode 12 to generate the heat needed for desorption. Due to the use of a circular array, as shown in FIG. 2, the overall pre-concentrator unit volume does not increase as fast as it would with a more linear arrangement of elements. Thus, it is possible to create a smaller form factor and/or use larger CDC foam element inserts.

In one case, the main housing wall 15 surrounds the elements and in one example the side wall 14 is about 0.11 inches and the pre-load spring wall 16 is about 0.26 inches as it provides an extra wall thickness to house the interior springs. In some cases, the electrode and insulator layer are about 0.13 inches. In some cases, the foam element dimensions are about 0.53×about 0.53×about 0.30 (thick) inches. A preliminary study focused on the volume of each element and determined that thinning the foam from 0.3" to 0.2" (while maintaining a length and a width at 0.53"×0.53") saved about 4.2 $cm^3$. A further reduction of the foam dimensions to 0.26"×0.26"×0.2" would increase the savings in volume down to about 125 mL. In one case, a further reduction in the overall volume was achieved (i.e., about 105 mL) by switching from a square packaging to a cylindrical packaging.

Referring to FIG. 2, a diagram of one embodiment of a radial arrangement for a multi-element, ultra-low SWaP chemical pre-concentrator 34 according to the principles of the present disclosure is shown. More specifically, the pre-concentrator is scalable to any number of foam elements. Here, four elements 22 are used to keep system volume low. As such, this embodiment is a circular array because of a resulting reduction in system volume. Additionally, this embodiment has no sliding seals, independent elements (for sequential desorption), no adjacent bleed, and a reduction in dead volume—less dilution of samples. In certain embodiments, a radial arrangement enables multiple foam units to be used for collection/desorption.

Still referring to FIG. 2, placement of four sampling elements 22 in a multi-element chemical pre-concentrator housing 20 is shown. Each element 22 is mounted in a cartridge comprising a foam element 4, dielectric/thermal insulators 2 and an elastomer seal 26. Each cartridge is installed in a main housing 20 and at the center of the housing there is a passageway 24 that guides motion of the top and the bottom covers (as described in FIGS. 3 and 4). Energized electrodes 28 are used to heat the foam element 4 during a desorption step. Each unit is controlled independently and is separately sealed during desorption to avoid bleed of the analytes to other chambers. The top and bottom plates (visible in FIG. 3 and FIG. 4) slide vertically to open the pre-concentrator 34 during sampling and close the pre-concentrator 34 during desorption. In this example there is an interface 36 to provide electrical power and control. According to one embodiment, the foam element 4 in each of the sampling elements 22 is the same. In a further embodiment, the foam elements 4 in the sampling elements are different in order to serve a broader spectrum of detection.

Figure 3:
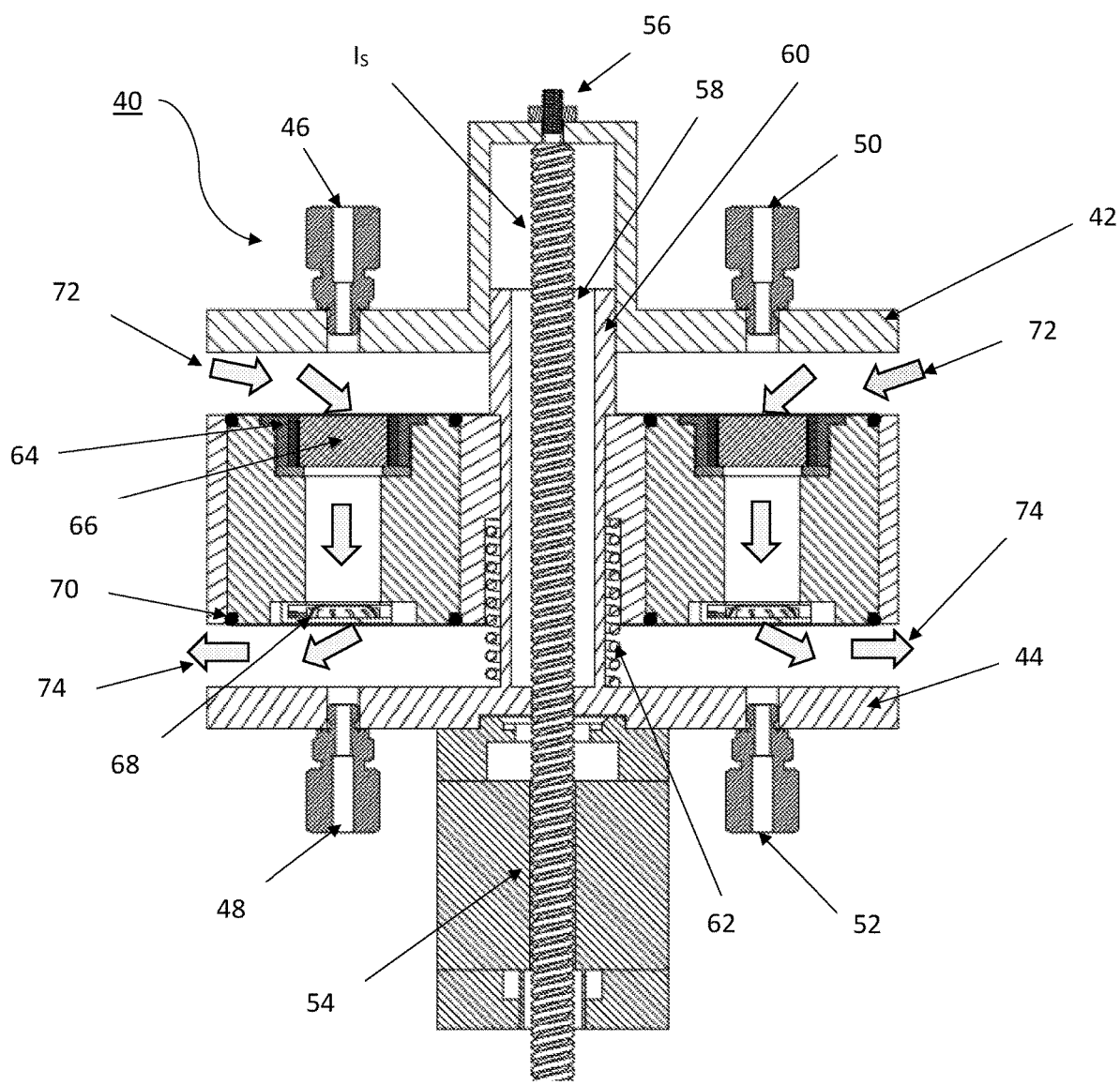
FIG. 3 is a cross-sectional view of one embodiment of a multi-element, ultra-low swap chemical pre-concentrator showing a concurrent adsorption step according to the principles of the present disclosure.

Referring to FIG. 3, a cross-sectional view of one embodiment of a multi-element, ultra-low SWaP chemical pre-concentrator 40 showing a concurrent adsorption step according to the principles of the present disclosure is shown. More specifically, in one embodiment, multiple CDC foam elements are packaged in a radial array configuration (See, e.g., FIG. 2). The top and bottom surfaces of the array are selectively capped or opened by use of a sliding caliper mechanism, by way of an actuator 54. This mechanism allows the CDC foam element array to be shifted between a sample collection (adsorb) (See, FIG. 3) and sample delivery (desorb) (See, FIG. 4) operational modes by use of a single linear actuator 54. In the adsorb position a low impedance air flow path input 72 and output 74 are provided so that ambient air can be independently drawn through each CDC element 66 to enable collection of the chemical sample. This low impedance airflow path enables both high flow and very low fan power consumption during sample collection.

Still referring to FIG. 3, a cross section of multi-element, ultra-low SWaP chemical concentrator 40 is shown with a linear actuator 54 used to expand a top cover 42 away from a bottom cover 44 to provide for gaps allowing a flow of air, or other gas, 72 and 74 to flow past the CDC foam element inserts 66. Here, fans or blowers 68 are used to push/pull the flow through the CDC foam element inserts. In this figure, 46 and 50 represent two of the connections to be used when attaching the pre-concentrator to an analyzer and 48 and 52 represent switched gas lines (not in use during adsorb stage).

FIG. 3 represents the multi-element chemical pre-concentrator 40 positioned in the adsorb position. Linear actuator 54 is driven to extend its lead screw which is guided in column 58 and retained to the top cover 42 by retaining nut 56. Journal bearing 60 slides within the chamber $I_s$ and guides the motion of the top cover 42 while coil spring 62 maintains equal travel of the bottom cover 44 by pulling the journal bearing 60 against the center housing. With the covers 42, 44 extended, low impedance air paths 72 and 74 are created for fans 68 which when energized draw air through the CDC foam elements 66 to enable sampling of the ambient air. CDC foam element thermal and electrical insulator 64 retains the foam element 66 in to the center housing. Both carrier gas delivery lines 48 and 52 and sample delivery lines 46 and 50 are deactivated during the sampling/adsorbing mode of operation.

Figure 4:
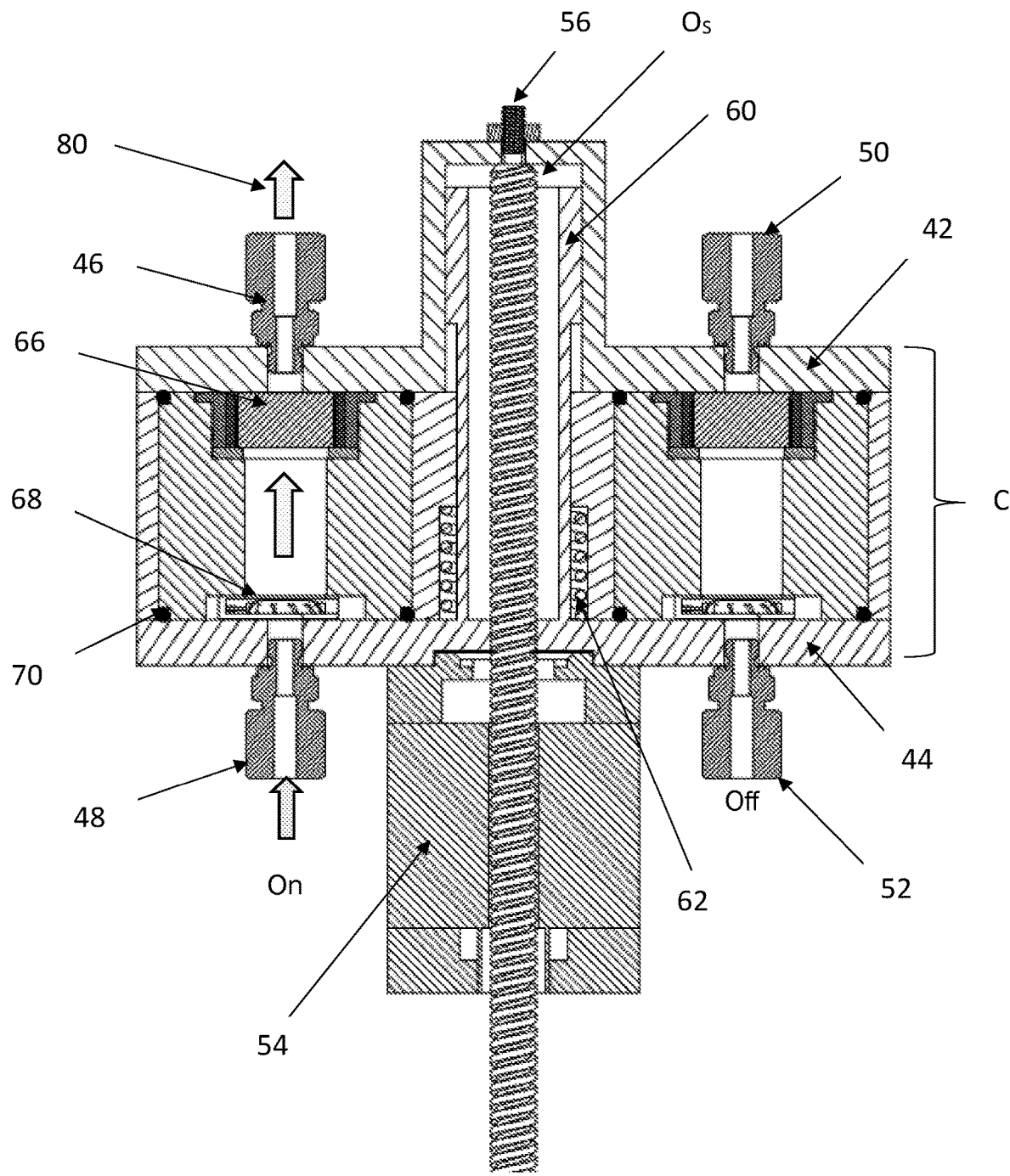
FIG. 4 is a cross-sectional view of one embodiment of a multi-element, ultra-low swap chemical pre-concentrator showing a sequential desorption step according to the principles of the present disclosure.

Referring to FIG. 4, a cross-sectional view of one embodiment of a multi-element, ultra-low SWaP chemical pre-concentrator showing a sequential desorption step according to the principles of the present disclosure is shown. More specifically, in the desorb mode the CDC element 66 is placed in a position having minimum dead volume where the chemical sample is released by heating of the CDC foam element through direct application of electric current. The minimal dead volume that is achieved during desorb serves to maximize the concentration of the sample bolus that is delivered to the chemical analyzer. Once the sample is desorbed, a switched gas valve (48, 52) delivers a burst of pressurized carrier gas to drive the sample towards the chemical analyzer inlet (46, 50).

FIG. 4 represents the multi-element chemical pre-concentrator positioned in the desorb position. Linear actuator 54 is driven to retract its lead screw which is guided in column 58 and retained to the top cover 42 by retaining nut 56. Journal bearing 60 slides within the chamber $O_s$ and guides the motion of the top cover 42 while coil spring 62 is compressed to enable closure of the bottom cover 44. Both the top and bottom covers 42, 40 form an air tight seal against the center housing by clamping against elastomer seals 70. With the top and bottom covers now sealed, the CDC foam elements 66 can be selectively heated by applying electric current while insulator 64 simultaneously minimizes the energy required for heating and directs electric current only through the foam element 66 via the opposing electrodes. Once the foam 66 is heated, carrier gas port 48 is switched "on" enabling gas containing analytes 80 to flow through the foam element 66 and out the sample delivery line 46 to the chemical analyzer (not shown).

In certain embodiments, energy consumption is directly linked to the volume of the foam as a first approximation. Therefore, a foam volume reduction will result in a commensurate energy consumption reduction. Such a volume reduction may induce a lower loading capacity or an earlier analyte breakthrough. Several options are available to compensate for such a potential drawback. For example, the depth of the foam can be increased to generate a longer flow path. Another alternative is to use a foam with a denser porosity, which will increase the overall surface area available for analyte interaction.

In some cases, to address an increase in background analyte levels, the effective loading of the foam is increased. First, increasing the porosity of the foams provides more surface area and therefore more binding sites for background analytes to enable the capture of more analytes. Second, increasing the CDC foam element layer can have similar effect in terms of providing more bonding sites. In some cases, an increase in sampling time is driven by the optimization of the duty cycle of the air sampling fan. The duty cycle can be modified and balanced against the energy consumption.

Figure 5:
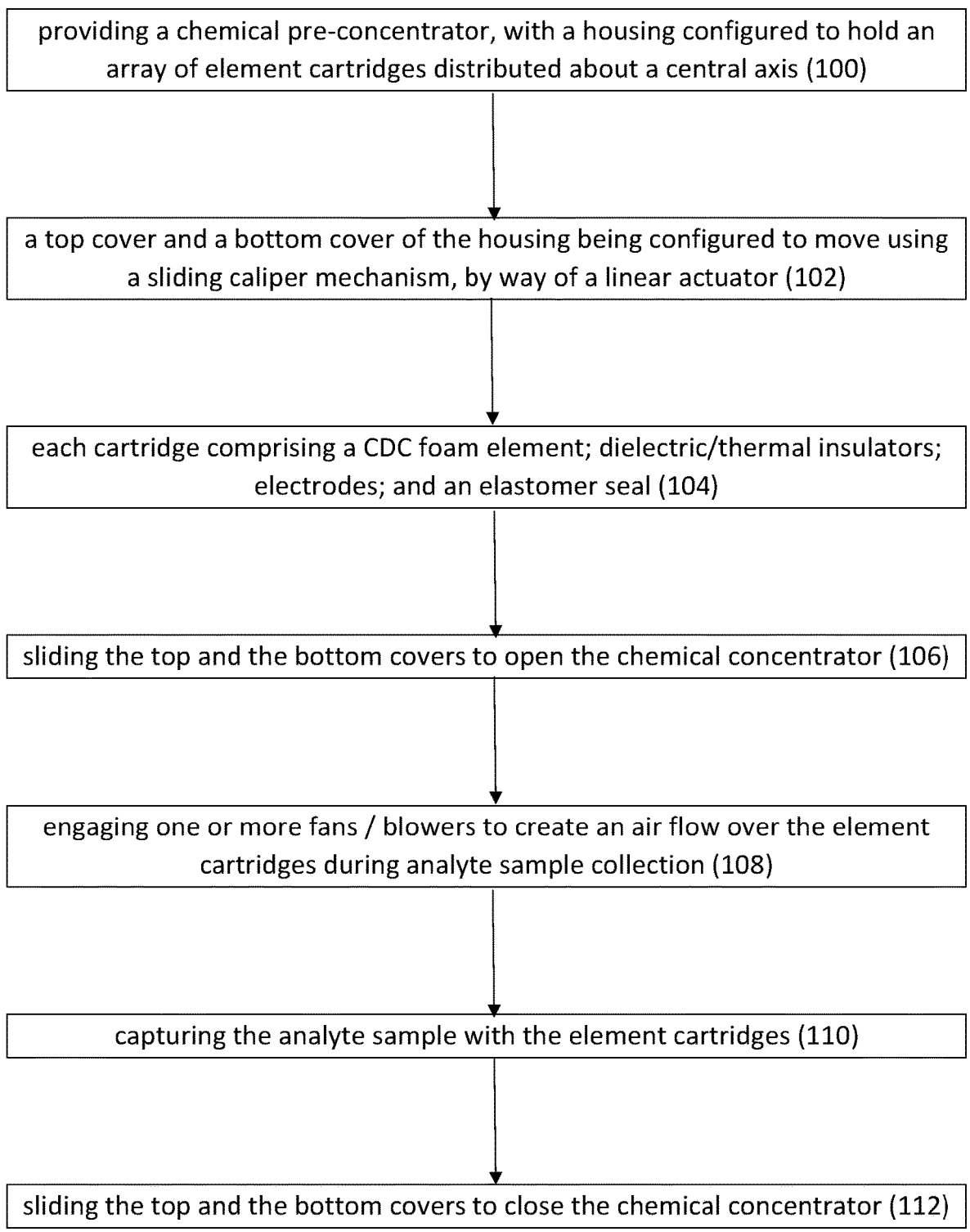
FIG. 5 is a flow chart of one embodiment of a method according to the principles of the present disclosure.

Referring to FIG. 5, a flow chart of one embodiment of a method according to the principles of the present disclosure is shown. More specifically, a method of collecting chemical analytes, comprises providing a chemical pre-concentrator, comprising: a housing configured to hold an array of chemical pre-concentrator element cartridges distributed about a central axis 100. In certain embodiments, the pre-concentrator has a top cover and a bottom cover configured to move using a sliding caliper mechanism, by way of a linear actuator 102. In certain embodiments, each cartridge comprises a CDC foam element, dielectric/thermal insulators, electrodes, and an elastomer seal 104. By sliding the top and the bottom covers, the chemical pre-concentrator opens 106. Engaging one or more fans or blowers to create an air flow over the element cartridges during analyte sample collection 108, enables capturing the analyte sample with the element cartridges 110. By sliding the top and the bottom covers of the chemical pre-concentrator, it is closed 112.

Figure 6:
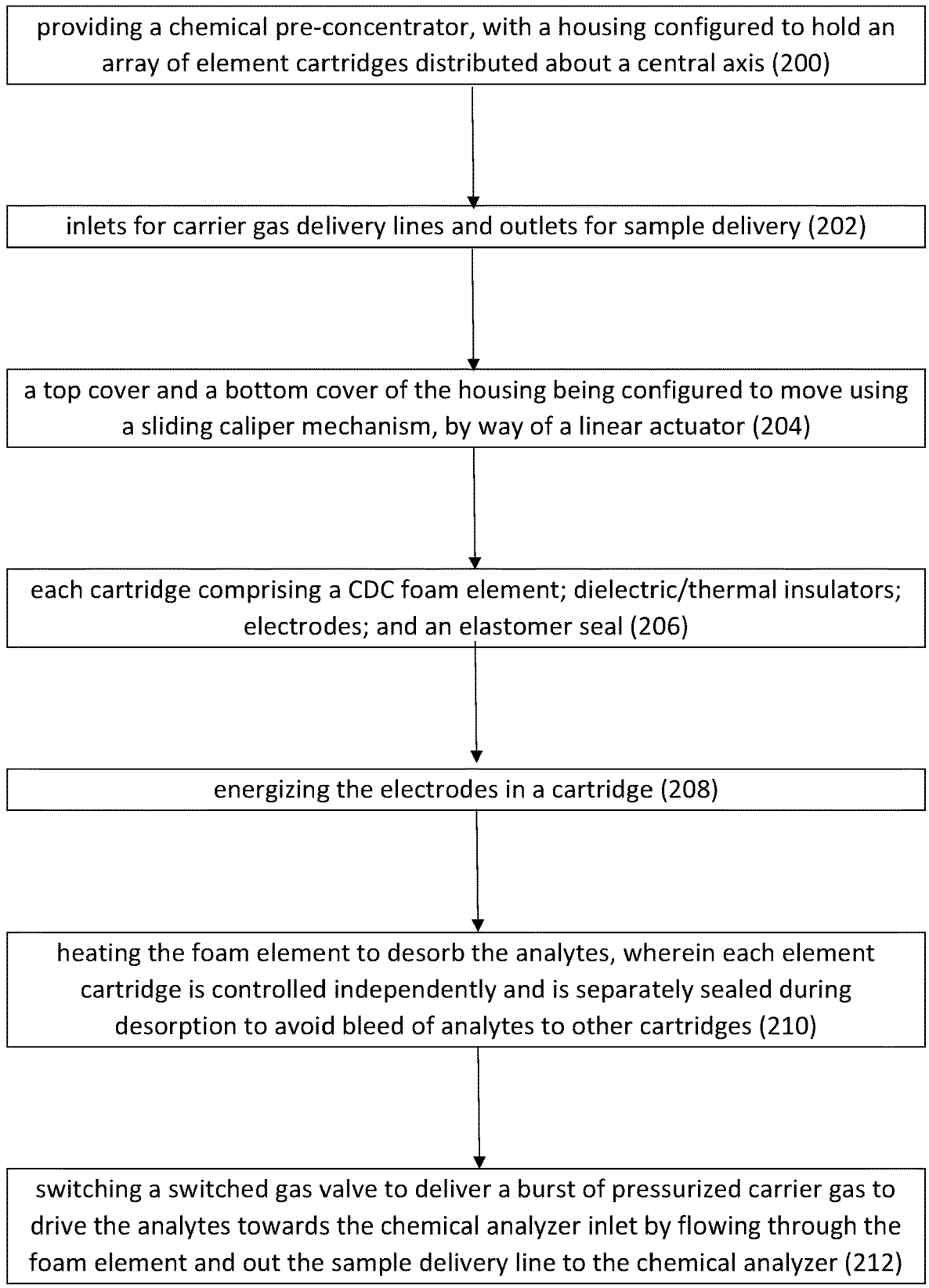
FIG. 6 is a flow chart of another embodiment of a method according to the principles of the present disclosure.

Referring to FIG. 6, a flow chart of another embodiment of a method according to the principles of the present disclosure is shown. More specifically, a method of delivering chemical analytes to a chemical analyzer for analysis, comprises providing a chemical pre-concentrator, having a housing configured to hold an array of chemical pre-concentrator element cartridges distributed about a central axis 200. In some embodiments, the pre-concentrator has inlets for carrier gas delivery lines and outlets for sample delivery 202 and a top cover and a bottom cover of the housing being configured to move using a sliding caliper mechanism, by way of a linear actuator 204. In some embodiments, each cartridge comprises CDC foam element, dielectric/thermal insulators, electrodes, and an elastomer seal 206. By energizing the electrodes in a cartridge 208 the foam elements are heated to desorb the analytes, wherein each element cartridge is controlled independently and is separately sealed during desorption to avoid bleed of analytes to other cartridges 210. By switching a switched gas valve to deliver a burst of pressurized carrier gas, the analytes are driven towards the chemical analyzer inlet by flowing through the foam element and out the sample delivery line to the chemical analyzer 212.

It will be appreciated from the above that the invention may be implemented as computer software, which may be supplied on a storage medium or via a transmission medium such as a local-area network or a wide-area network, such as the Internet. It is to be further understood that, because some of the constituent system components and method steps depicted in the accompanying Figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

The computer readable medium as described herein can be a data storage device, or unit such as a magnetic disk, magneto-optical disk, an optical disk, or a flash drive. Further, it will be appreciated that the term "memory" herein is intended to include various types of suitable data storage media, whether permanent or temporary, such as transitory electronic memories, non-transitory computer-readable medium and/or computer-writable medium.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a limitative sense.

The foregoing description of the embodiments of the present disclosure has been presented for the purposes of illustration and description. It is not intended to be exhaustive or to limit the present disclosure to the precise form disclosed. Many modifications and variations are possible in light of this disclosure. It is intended that the scope of the present disclosure be limited not by this detailed description, but rather by the claims appended hereto.

A number of implementations have been described. Nevertheless, it will be understood that various modifications may be made without departing from the scope of the disclosure. Although operations are depicted in the drawings in a particular order, this should not be understood as requiring that such operations be performed in the particular order shown or in sequential order, or that all illustrated operations be performed, to achieve desirable results.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. Modifications and substitutions by one of ordinary skill in the art are considered to be within the scope of the present disclosure.

What is claimed:

1. A chemical pre-concentrator, comprising:
   a housing configured to hold an array of chemical pre-concentrator element cartridges distributed about a central axis; and
   a top cover and a bottom cover of the housing being configured to move using a sliding caliper mechanism, by way of a linear actuator;
   each chemical pre-concentrator element cartridge comprising:
   a carbide derived carbon foam element;
   dielectric/thermal insulators;
   electrodes; and
   an elastomer seal;
   wherein the top and the bottom covers slide to open at least one of the chemical pre-concentrator element cartridges during analyte sample collection and to close the at least one chemical pre-concentrator element cartridge for analyte sample delivery, wherein the electrodes of the at least one chemical pre-concentrator element cartridge are energized by a power source such that the at least one chemical pre-concentrator element cartridge heats the carbide derived carbon foam element and causes the carbide derived carbon foam element to desorb analytes sample, and each of the at least one chemical pre-concentrator element cartridge is controlled independently and is separately sealed during desorption to avoid bleed of analyte samples to other chemical pre-concentrator element cartridges; and wherein the at least one chemical pre-concentrator element cartridge further comprises a series of springs with pre-loaded adjustments to facilitate pressing spring pressure plates against thermal insulators on each side of the carbide derived carbon foam element of the at least one chemical pre-concentrator element cartridge, to cause a pair of energized electrodes to contact the carbide derived carbon foam element of the at least one chemical pre-concentrator element cartridge during a desorption step.

2. The chemical pre-concentrator according to claim 1, wherein the linear actuator is used to expand the top cover away from the bottom cover to provide for gaps allowing a flow of air, or other gas, to flow past the element cartridges.

3. The chemical pre-concentrator according to claim 1, wherein the array comprises four element cartridges.

4. The chemical pre-concentrator according to claim 1, wherein during analyte sample collection an air flow path is provided so that ambient air can be independently drawn through each element cartridge to enable collection of the analyte samples.

5. The chemical pre-concentrator according to claim 1, further comprising fans/blowers to push/pull air flow through the element cartridges.

6. The chemical pre-concentrator according to claim 1, further comprising inlets for carrier gas delivery lines and outlets for sample delivery lines used when attaching the pre-concentrator to an analyzer.

7. A method of collecting chemical analytes, comprising:
providing a chemical pre-concentrator, comprising:
a housing configured to hold an array of chemical pre-concentrator element cartridges distributed about a central axis; and
a top cover and a bottom cover of the housing being configured to move using a sliding caliper mechanism, by way of a linear actuator;
each chemical pre-concentrator element cartridge comprising:
a carbide derived carbon foam element;
dielectric/thermal insulators;
electrodes;
an elastomer seal; and
a series of springs with pre-loaded adjustments to facilitate pressing spring pressure plates against thermal insulators on each side of the carbide derived carbon foam element of the chemical pre-concentrator element cartridge, to cause a pair of energized electrodes to contact the carbide derived carbon foam element of the chemical pre-concentrator element cartridge during a desorption step;
wherein the top and the bottom covers slide to open the chemical pre-concentrator element cartridge during analyte sample collection and to close the chemical pre-concentrator element cartridge for analyte sample delivery, wherein the electrodes of the chemical pre-concentrator element cartridge are energized by a power source such that the chemical pre-concentrator element cartridge heats the carbide derived carbon foam element and causes the carbide derived carbon foam element to desorb analytes sample, and the chemical pre-concentrator element cartridge is controlled independently and is separately sealed during desorption to avoid bleed of analyte samples;
sliding the top and the bottom covers to open the chemical pre-concentrator;
engaging one or more fans/blowers to create an air flow over at least one of the chemical pre-concentrator element cartridges during analyte sample collection;
capturing analyte samples with the carbide derived carbon foam element of at least one chemical pre-concentrator element cartridge; and
sliding the top and the bottom covers to close the chemical pre-concentrator.

8. The method of collecting chemical analytes according to claim 7, wherein the array comprises four element cartridges.

9. The method of collecting chemical analytes according to claim 7, wherein the linear actuator is used to expand the top cover away from the bottom cover to provide for gaps allowing a flow of air, or other gas, to flow past the element cartridges.

10. The method of collecting chemical analytes according to claim 7, wherein during analyte sample collection an air flow path is provided so that ambient air can be independently drawn through each element cartridge to enable collection of analyte samples.

11. The method of collecting chemical analytes according to claim 7, wherein the chemical pre-concentrator further comprises inlets for carrier gas delivery lines and outlets for sample delivery lines used when attaching the chemical pre-concentrator to an analyzer.

12. A method of delivering chemical analytes to a chemical analyzer for analysis, comprising:
providing a chemical pre-concentrator, comprising:
a housing configured to hold an array of chemical pre-concentrator element cartridges distributed about a central axis;
inlets for carrier gas delivery lines and outlets for sample delivery; and
a top cover and a bottom cover of the housing being configured to move using a sliding caliper mechanism, by way of a linear actuator;
each chemical pre-concentrator element cartridge comprising:
a carbide derived carbon foam element;
dielectric/thermal insulators;
electrodes; and
an elastomer seal; and
wherein at least one of the chemical pre-concentrator element cartridges further comprises a series of springs with pre-load adjustments to facilitate pressing spring pressure plates against the dielectric/thermal insulators on each side of the carbide derived carbon foam element of the at least one of the chemical pre-concentrator element cartridges, to cause a pair of energized electrodes to contact the carbide derived carbon foam element of the at least one of the chemical pre-concentrator element cartridges in a desorption step;

energizing the electrodes in a at least one chemical pre-concentrator element cartridge;

heating the carbide derived carbon foam element of the at least one chemical pre-concentrator element cartridge to desorb the analytes; and switching a switched gas valve to deliver a burst of pressurized carrier gas to drive the analytes towards a chemical analyzer inlet by flowing through the carbide derived carbon foam element of at least one chemical pre-concentrator element cartridge and out a sample delivery line to the chemical analyzer, wherein each chemical pre-concentrator element cartridge is controlled independently and is separately sealed during desorption to avoid bleed of analytes.

13. The method of delivering chemical analytes to a chemical analyzer for analysis according to claim 12, wherein the dielectric/thermal insulator of at least one chemical pre-concentrator element cartridge is used around the carbide derived carbon foam element to reduce heat loss from the carbide derived carbon foam element.

14. The method of delivering chemical analytes to a chemical analyzer for analysis according to claim 12, wherein the temperature applied to the carbide derived carbon foam element of at least one chemical pre-concentrator element cartridge for desorption is about 350° C.

15. The method of delivering chemical analytes to a chemical analyzer for analysis according to claim 12, further comprising fans/blowers to push/pull air flow through the element cartridges.

16. The method of delivering chemical analytes to a chemical analyzer for analysis according to claim 12, wherein the array comprises four element cartridges.

\* \* \* \* \*